(12) United States Patent
Juarez et al.

(10) Patent No.: US 10,470,465 B2
(45) Date of Patent: *Nov. 12, 2019

(54) ***GLOMUS IRANICUM* VAR. *TENUIHYPHARUM* VAR. NOV. STRAIN AND USE THEREOF AS BIOSTIMULANT**

(71) Applicant: SYMBORG, S.L., Murcia (ES)

(72) Inventors: Jesus Juarez, Murcia (ES); Felix Fernandez, Murcia (ES)

(73) Assignee: SYMBORG, S.L., Murcia (ES)

(*) Notice: Subject to any disclaimer, the term of this patent is extended or adjusted under 35 U.S.C. 154(b) by 0 days.

This patent is subject to a terminal disclaimer.

(21) Appl. No.: 15/889,731

(22) Filed: Feb. 6, 2018

(65) Prior Publication Data

US 2018/0168167 A1 Jun. 21, 2018

Related U.S. Application Data

(63) Continuation of application No. 15/034,072, filed as application No. PCT/EP2014/057043 on Apr. 8, 2014, now abandoned.

(30) Foreign Application Priority Data

Jul. 2, 2013 (EP) .................................. 13174708

(51) Int. Cl.

| | | |
|---|---|---|
| *A01N 63/04* | (2006.01) | |
| *C12N 1/14* | (2006.01) | |
| *A01H 17/00* | (2006.01) | |
| *C12R 1/645* | (2006.01) | |

(52) U.S. Cl.
CPC ............ *A01N 63/04* (2013.01); *A01H 17/00* (2013.01); *C12N 1/14* (2013.01); *C12R 1/645* (2013.01)

(58) Field of Classification Search
CPC ...................................................... C12R 1/645
See application file for complete search history.

(56) References Cited

FOREIGN PATENT DOCUMENTS

| EP | 0314439 A2 | 5/1989 |
|---|---|---|
| EP | 1840110 A1 | 10/2007 |
| ES | 2364684 A1 | 9/2011 |

OTHER PUBLICATIONS

J. Blaszkowski, et al; *Glomus africanum* and *G. iranicum*, two new species of arbuscular . . . ; Mycologia; vol. 102; No. 6; 2010; pp. 1450-1462; XP-002713888.

E. Neumann, et al; Colonisation with the arbuscular mycorrhizal fungus *Glomus mosseae* . . . ; Plant and Soil; vol. 261; 2004; pp. 245-255.

R. Busby, et al; Arbuscular mycorrhizal fungal community differs between a coexisting native shrub and . . . ; Mycorrhiza; vol. 23; 2013; pp. 129-141.

International Search Report dated Jun. 16, 2014 for PCT/EP2014/057043.

*Primary Examiner* — Bin Shen

(74) *Attorney, Agent, or Firm* — Lucas & Mercanti, LLP

(57) ABSTRACT

*Glomus iranicum* var. *tenuihypharum* var. nov. strain deposited under BCCM deposit number 54871, comprising the sequence identified by SEQ ID NO: 1; composition having the strain and 2:1 smectite clays and use thereof as biostimulant. The invention also discloses a composition having the strain, fungicides, bio-fungicides, insecticides, bio-insecticides, nematicides and bio-nematicides.

17 Claims, No Drawings
Specification includes a Sequence Listing.

GLOMUS IRANICUM VAR. TENUIHYPHARUM VAR. NOV. STRAIN AND USE THEREOF AS BIOSTIMULANT

CROSS-REFERENCE TO RELATED APPLICATIONS

This Application is a continuation of U.S. application Ser. No. 15/034,072, filed on May 3, 2016, which in turn is a 371 of PCT/EP2014/057043, filed on Apr. 8, 2014, which claimed the priority of European Patent Application No. 13174708.1 filed on Jul. 2, 2013, each of which are incorporated herein by reference.

FIELD OF THE INVENTION

The invention relates to the agronomic field. Specifically, the present invention relates to a composition comprising a *Glomus iranicum* var. *tenuihypharum* var. nov. strain and other components, which is used as bio-stimulant.

BACKGROUND OF THE INVENTION

Mycorrhizal compositions made so far have a natural limit of mycorrhizal propagules. Said limit is mainly due to the strain used and the method for obtaining the mycorrhizal compositions. Not all species of mycorrhizal fungi found in the literature have a constant and positive mycorrhizal activity in crops.

Mycorrhiza-forming fungi described in the state of the art do not provide a consistently positive impact on crop yield due to a lack of efficiency in mycorrhizal colonization under all soil conditions and fertility levels. The high level of mycorrhizal colonization and growth of mycelium demonstrated by the strain described in the present application under a wide range of soil saline conditions will allow a more widespread use of this technology in intensive agriculture, resulting in improved efficiency in water use, nutrient uptake, overall yield of the crop and growth. Further, this strain has shown beneficial effects in combination with high levels of fertilization.

DESCRIPTION OF THE INVENTION

One embodiment invention is a strain of *Glomus iranicum* var. *tenuihypharum* var. nov. deposited under BCCM deposit number 54871, comprising the sequence identified by SEQ ID NO: 1, hereinafter strain of the invention.

*Glomus iranicum* var. *tenuihypharum* var. nov. strain of the invention, isolated from a Solonetz Gley saline sodic soil in the town of Fortuna, Murcia (Spain), was deposited on 19 Apr. 2013 at the international depositary authority Belgian Coordinated Collections of Micro-Organisms (BCCM) with the address at Université Catholique de Louvain, Mycothèque de l'Université catholique de Louvain (MUCL), Croix du Sud 2, Box L7.05.06, 1348 Louvain-la-Neuve, by Symborg, S.L., with address at Ceeim Building, University Campus, S/N, 30100 Murcia, Spain.

The *Glomus iranicum* var. *tenuihypharum* var. nov. strain has been identified by the depositor by the reference SYM-BORG-001, and received the deposit number 54871 by the international depositary authority.

The sporocarps of the *Glomus iranicum* var. *tenuihypharum* var. nov. strain of the invention are unknown. Said strain spores occur singly or in loose clusters in the soil and they can also be formed sporadically in the roots. Spores are hyaline to ocher light, with subglobose to globular shape (rarely irregular), relatively small (24.0) 30.7±3.7 (42) microns in diameter, composed of two layers of wall (1-4 m thick) an interior laminated compact layer (0.5-1.5 m), and an outer semi-permanent layer, roughened in young spores and somewhat rough appearance in adult spores and larger than 0.5 to 2.0 m thick. The walls of the interior spore of young spores have a reddish brown staining with Melzer's reagent, but the color disappears on the staining of mature spores, the contents of the spores have a pale appearance. The hypha that holds the spore has a hyaline to pale ocher color, is straight or wavy of 2.5 to 4.5 micron in diameter (average of 3.0 micron), cylindrical and with a slight funnel shape which merges with the open-pored layers of the spore wall, at least in mature spores. Germination Structure: germ tube that grows and develops back through the union of the hypha with the spore. It forms vesicular arbuscular mycorrhizae.

The mycelium forms an extensive network. The extramatrical mycelium is hyaline to pale yellow, profuse and the spores appear always in the soil matrix, forming abundant sporocarps in group (2 to 8 individual spores). The unique feature of this species is the large amount of external mycelium network and the inability to grow under in vitro association of transformed roots.

The strain was isolated from a Solonetz Gley type saline soil. The main feature of these soils is that they are very hydromorphic, very compact and with a lot of salt deposits on the surface.

The strain was isolated from a soil located in the town of Fortuna, Murcia (Spain).

The following table shows some chemical properties of the original soil where the *Glomus iranicum* var. *tenuihypharum* var. nov. strain was isolated.

TABLE 1

| Soil properties | |
| --- | --- |
| Parameters | Values |
| pH ($H_2O$) | 8.5 |
| $CaCO_3$ (%) | 12 |
| C/N | 6.5 |
| $Ca^{++}$ (ppm) | 5809.6 |
| $Mg^{++}$ (ppm) | 2,967.04 |
| $K^+$ (ppm) | 2955 |
| $Na^+$ (ppm) | 1829.4 |

According to a phylogeny based on 813 base pairs of the ribosomal RNA 18S (partial sequence), ITS1 (internal transcribed spacer 1, complete sequence) genes and the ribosomal RNA 5.8S (partial sequence) gene, the strain of the invention is categorized into a clade consisting of *Rhizophagus* (before *Glomus* Ab group, represented by *Rhizophagus irregularis*, *Glomus intraradices* and *Rhizophagus bistratum*).

According to this phylogeny *Glomus indicum* and *Glomus achrum* are the closest relatives. Around fifty sequences of uncultured *Glomus* spp. clones can be found with a high identity (99%) to the sequence of the strain of the invention in the NCBI server (gene bank).

It appears therefore that the new taxon has a cosmopolitan distribution and a wide host range. Very similar sequences have originated in Japan (Ogura-Tsujita Y. et al. 2013. Arbuscular mycorrhiza formation in cordate gametophytes of two ferns, *Angiopteris lygodiifolia* and *Osmunda japonica*. Journal of Plant Research. 126 (1): 41-50; Yamato M. et al. 2011. Arbuscular mycorrhizal fungi in roots of nonphotosynthetic plants, *Sciaphila japonica* and *Sciaphila*

*tosaensis* (Triuridaceae). *Mycoscience* 52: 217-223.), New Zealand, Africa and North America (Appoloni S. et al. 2008. Molecular community analysis of arbuscular mycorrhizal fungi in roots of geothermal soils in Yellowstone National Park (USA). *Microbial Ecology* 56 (4): 649-659).

The most striking morphological character of the strain of the invention is the small size of the spores and the hyaline to very light ocher coloration and that they occur singly or in small groups on the soil.

The only strain of *Glomus* sp. with hyaline spores that are similar in size and color to the strain of the invention is *Glomus iranicum* (Blaszkowski J et al. (2010). *Glomus africanum* and *G. iranicum*, two new species of arbuscular mycorrhizal fungi (Glomeromycota). *Mycologia* 102: 1450-1462.) (Table 1). The three layers of the wall of the spores are morphologically indistinguishable from that of the strain of the invention. There is a clear difference in the strain of the invention and it is that the size of their hyphae attached to the spore is very fine.

The outer wall L1 of spores of *Glomus iranicum* (Blaszkowski J et al. (2010). *Glomus africanum* and *G. iranicum*, two new species of arbuscular mycorrhizal fungi (Glomeromycota). *Mycologia* 102: 1450-1462.) deteriorates rapidly and consistently, with strong dextrinoid activity, however in the case of the strain of the invention, it is only observed in very young spores, thus it is concluded that it is a variety of *Glomus iranicum* and we propose the new variety *tenuihypharum*.

It is a strain that adapts to and tolerates perfectly saline environments and fertilizer solutions with high electrical conductivities.

The species produces abundant extramatrical mycelium, which ensures proper symbiotic functioning.

The species reaches high concentrations of internal colonization in short periods of time, especially in crops under intensive agriculture, indicating a high effectiveness of performance under these conditions.

Due to the small size of their spores and abundant extramatrical mycelium, as well as the recovery capacity of the same due to physical damage, the strain can be handled and ground to below 80 microns, remaining totally viable on a clay substrate for more than two years and a proven effectiveness in a range of $1.2 \times 10^4$ to $1 \times 10^8$ infective propagules/100 ml$^{-1}$ of soil.

The application of this species promotes an effective response in productivity of crops under intensive agriculture, and keeps high levels of physiological activity at the expense of a low energy cost, given by the low rates of transpiration that promote high and efficient use of the water.

The strain promotes a radical change of the root architecture, promoting a different root system, horizontal and with greater dichotomy induced by quick internal and external mycorrhizal colonization, and the need for greater amount of host root cells, which also promote a greater development of roots in the short and long term.

Another important aspect to be assessed is the microbial activity generated by this organism in the rhizosphere system. This strain produces a constant stimulation of the rhizospheric microbiota in the treated plants. This fact is due to the own exudation of nutritional elements through the rootlets, mycorrhizae and hyphae stimulating both micorizosphere and rhizosphere activity in the vicinity of the external mycelium of the *Glomus iranicum* var. *tenuihypharum* var. nov. strain, which produces a higher microbial concentration at each of the moments tested.

*Glomus iranicum* var. *tenuihypharum* var. nov. is a species of excellent mycorrhiza-forming fungus.

One embodiment of the invention is a composition, hereinafter composition of the invention, comprising a strain of *Glomus iranicum* var. *tenuihypharum* var. nov. deposited under BCCM deposit number 54871 comprising the sequence identified by SEQ ID NO: 1 and 2:1 smectite clays. In particular, said 2:1 smectite clays are dioctahedral or trioctahedral. Also in particular, said 2:1 smectite clays are selected from the group consisting of sepiolite, attapulgite, nontronite and saponite.

The present invention utilizes clay of the dioctahedral or trioctahedral smectite, sepiolite and attapulgite type, all with high plasticity when wetted and consisting of a very fine granular material, consisting of very small particles the size of which is less than 4 microns, and its main property is the expansion in systems with low water availability as it may be a substrate for mycorrhizal fungi reproduction. On the other hand, it is very important the colloid formation and disintegration in the presence of abundant water when applied in localized irrigation systems. These types of clays upon completion of one of the production phases of the inoculant, provide the mycorrhizal propagules with: spores, extramatrical mycelium and colonized rootlets; stressful situations that promote subsequent acceleration of the germination processes once inoculated under intensive and ecological crops conditions.

In example 1 of the invention it was found that the effects promoted by the *Glomus iranicum* var. *tenuihypharum* var. nov. strain, in all the variables studied were higher than those found in the species *Glomus mosseae* and *Glomus intraradices*

Due to its mycorrhizal expression, it is good to highlight the rich and significant production of extramatrical mycelium and of easily extractable Glomalin that occurs in the presence of the species *Glomus iranicum* var. *tenuihypharum* var. nov. regardless of the fertilization used, indicative of the adaptation of this microorganism to various saline environments.

The plants treated with *Glomus iranicum* var. *tenuihypharum* var. nov. exhibit increased production of leaf and root biomass, related in turn to a higher concentration of nutrients in leaves in the presence of the largest fertilizer dosages, indicative of the high tolerance to these conditions.

Plants treated with 100% of fertirrigation in the presence of the *Glomus mosseae* and *Glomus intraradices* strains, produced no significant difference compared with control plants in terms of fresh biomass production. Their activity was decreased from the increase in the doses of fertilizers.

The application of *Glomus iranicum* var. *tenuihypharum* var. nov. produces high photosynthetic activity at the expense of lower rates of perspiration, which leads the treated plants to make a more efficient use of water throughout the crop, both at doses of 50% and of 100% of the fertilizer applied.

*Glomus iranicum* var. *tenuihypharum* var. nov. strain has high activity relative to the rest of inoculants used in Example 1, possibly derived from the nature of the species itself, highly symbiotic, superproducer of extramatrical mycelium, Glomalin and a strong interior colonization, which in turn produces an adequate physiological activity with low stomatal conductance, leading to an efficient use of water with high productivity, even with higher doses of fertilizer.

Another embodiment is the composition of the invention, wherein the concentration of said *Glomus iranicum* var. *tenuihypharum* var. nov. strain is between 0.05 and 4% by weight. In particular, said concentration is between 0.1 and 3% by weight.

Another embodiment is the composition of the invention, wherein the form of presentation of said composition is powder, emulsifiable concentrate or granules.

Another embodiment is the composition of the invention, wherein said composition is a liquid, a solid or a gel.

Another embodiment is the composition of the invention comprising at least one fungicide, at least one bio-fungicide, at least one insecticide, at least one bio-insecticide, at least one nematicide and/or at least one bio-stimulant.

In particular, said fungicide is selected from the group consisting of Maneb, Mancozeb, Metalaxyl-Ridomil, Myclobutanil, Olpisan, Propamocarb, Quintozene, Streptomycin, Sulfur, Thiophanate-methyl, Thiram, triforine, vinclozolin, Zinc white, Zineb, Ziram, Banrot, Fixed copper, Chlorothalonil, Chlorothalonil, Captan, Chloroneb, Cyproconazole, Zinc ethelene, bisdithiocarbamate, Etridiazole, Fenaminosulf, Fenarimol, Flutolanil, Folpet, Fosetyl-AL and Iprodione.

In particular, said bio-fungicide is selected from the group consisting of *Trichodermas* sp, *Bacillus subtilis*, *Bacillus licheniformis*, *Bacillus pumilus*, *Bacillus amyloliquefaciens*, *Streptomyces* sp, *Coniothyrium minitans* and *Pythium oligandrum*.

In particular, said insecticide is selected from the group consisting of organophosphate, carbamate and neonicotinoid.

In particular, said bio-insecticide is selected from the group consisting of *Bacillus* sp., *Chromobacterium* sp., *Beauveria* sp. and *Metarhizium* sp.

In particular, said nematicide is organophosphate or carbamate.

In particular, said bio-nematicide is *Pasteuria* sp.

Another embodiment is a method for obtaining the composition of the invention, comprising:
(a) coating inoculation of a seed of a host plant with *Glomus iranicum* var. *tenuihypharum* var. nov. deposited under BCCM deposit number 54871,
(b) cultivating said plant in watering cycles of between 7 to 10 days on a reproduction substrate comprising smectite clays in a percentage above 52% of the total weight of said substrate,
(c) discontinuing said watering for a period equal to or greater than 20 days, (d) removing the aerial part of the plant and removing the substrate and
(e) milling said substrate below 80 microns at a temperature between 25 and 30° C. to obtain said composition.

Another embodiment is the use of the composition of the invention as bio-stimulant.

The strain of the invention exerts the function of translocation of nutrients, taking these nutrients from the soil or substrate and using said nutrients in its metabolic system, it translocates said nutrients from its mycelium network and it subsequently exchanges them in the root cells. This phenomenon can be described by the term biostimulation and that is why one of the embodiments of the invention is the use of the mycorrhizal composition of the invention as bio-stimulant.

In the present specification it should be construed that the term "fertilizer" is within the scope of the broader term "bio-stimulant".

Another embodiment is the use of the invention, wherein the composition of the invention is applied to the plant by seed treatment, root treatment, roots embedded in an emulsion, addition to irrigation water, irrigation, application of powder to the root system or application of emulsion injected into the root system.

Preferred Embodiments

Example 1

Genetic Identification of the Strain of the Invention

DNA Extraction

Isolated hyphae and spores were transferred to 1.5 ml Eppendorf tubes with 0.2 g of glass beads (2 mm diameter) and 100 μL of CTAB buffer (2% CTAB=Cetyl trimethyl ammonium bromide, 1.4 M NaCl, 0.1 M Tris-HCl pH 7.5, 0.2 M Na-EDTA).

This mixture was homogenized using a ball mill type Retsch MM301 at full speed for 30 seconds. Another 400 μL of CTAB buffer were added and the mixture was incubated at 65° C. for one hour. Subsequently 400 μL of Cholroformo-isoamyl alcohol (24:1) were added and it is mixed by inverting the reaction tubes and then it was centrifuged for 5 min at 10,000×g, and the upper layer was recovered in a clean Eppendorf tube. This step was repeated twice. 200 μL of 5 M ammonium acetate were added to this suspension, the mixture was incubated at 4° C. for 30 minutes, followed by 20 minutes of spinning at 4° C. and 13,000 rpm. The DNA was precipitated with 700 μL of isopropanol at −20° C. overnight. The DNA pellet obtained was precipitated with isopropanol and washed with 70% ice-cold ethanol, air dried and re-dissolved in 50 μL of Tris ethylene diamine buffer (10 mM Tris, 10 mM EDTA, pH 8)+4.5 U RNase/ml.

PCR Conditions

The primers used for PCR amplification and for sequencing the internal transcribed spacers region of the 18S rDNA gene were Glom1310 and ITS4i (Redecker, 2000). Amplifications were performed in 0.2 mM dNTP-mix, 1 mM of each primer, 10% of PCR reaction buffer and double distilled sterile water. GoTaq® DNA polymerase (Promega, Mannheim, Germany) was added to 3.75 u/100 μL of reaction mixture; 2 μL of genomic DNA template was used in each 20 μL/reaction. Amplifications were carried out in a advanced thermal cycler Primus 96—(peqLab Biotechnology) in 200 reaction tubes mu 1 (94° C., 120 s initial denaturation, followed by 30 cycles of 94° C. 15 s, 52° C., 30 s, 72° C., 45 s, and a final slope at 72° C. for 120 s).

Data Analysis

The alignment was carried out initially using the computer program BioEdit 7.0. Phylogenetic analysis by maximum likelihood (ML) were carried out with the PHYML program. The nucleotide substitution model GTR was used with ML estimates of the base frequencies. The proportion of invariable sites were estimated and optimized. Four categories of the substitution rate were developed and the gamma distribution parameter was also estimated and optimized. Bootstrap analysis was used with 100 replicates to test the statistical support of the branches.

Sequencing

Excess primers and dNTPs were removed by column chromatography (Microspin S-300 HR, Amersham Biosciences). For partial sequencing of the 18S-ITS1-5.8S region primers Glom1310 and ITS4i were used in a concentration of 1.6 mM. Sequencing was carried out with PRISM BigDye™ Terminator Cycle Sequencing Kit from ABI (Applied Biosystems) according to the manufacturer's recommendations. The parameters for sequencing were delay 18 seconds at 96° C., followed by 25 cycles with 18 sec at 96° C., 5 seconds at 50° C. and 4 mM at 60° C. Sequence analysis was performed using an automated sequence analyzer (ABI PRISM 3130, Applied Biosystems) in conjunction with the ABI Prism™ Auto Assembler software (version 140, Applied Biosystems).

Ribosomal RNA 18S sequence (partial sequence), ITS1 (complete sequence) and ribosomal RNA 5.8S gene (partial sequence) were obtained from the strain of the invention, which sequence is identified by SEQ ID NO: 1.

Example 2

Effectiveness of the Composition of the Invention on Lettuce Crop

The plant species studied was "Roman" type *Lactuca sativa* L, annual plant with a growing cycle of 90 days. The seeding was performed by transplant in the January-March period, in pots of 75 cm×15 cm×15 cm in size, placing three seedlings/pot. The data of the chemical analysis of the soil used in the test are shown below (Table 2).

TABLE 2

Main features of the soil used in the test.

| Elements | Contents |
|---|---|
| Organic Matter (%) | 1.3 |
| Total Nitrogen (%) | 0.2 |
| C:N Ratio | 6.4 |
| Total Carbonates (%) | 10.2 |
| Active Limestone (%) | 2.6 |
| Assimilable phosphates (ppm) | 231.2 |
| Chlorides (meq/100 g) | 0.09 |
| Sulfates (meq/100 g) | 0.3 |
| Assimilable iron (ppm) | 25.2 |
| Assimilable copper (ppm) | 2.3 |
| Assimilable Manganese | 32.0 |
| Assimilable Zinc (ppm) | 1.2 |

Three species of mycorrhiza-forming fungi we used in this study: *Glomus mosseae* (Nicholson & Gerdeman) Gerdeman & Trappe, *Glomus intraradices* (NC Schenck & GS Sm. 1982) and *Glomus iranicum* var. *tenuihypharum* var. nov.

The method for obtaining the inoculants consisted of the propagation of the different *Glomus* species in a clay mineral substrate with the perennial host plant *Lollium* for 5 months. At the end of the life cycle of the plant species, the root system and the mycorrhizal propagules, spores, mycelium and colonized rootlets were homogenized and applied at the rate of 2 grams per plant.

The final concentration of the strains was: *Glomus mosseae:* 45 spores $g^{-1}$ and 123 mg extramatrical mycelium $g^{-1}$, *Glomus intraradices:* 166 spores $g^{-1}$ and 200 mg extramatrical mycelium $g^{-1}$ and *Glomus iranicum* var. *tenuihypharum* var. nov., 200 spores $g^{-1}$ and 430 mg extramatrical mycelium $g^{-1}$ (as determined by the methods of Giovannetti et Mosse, 1980; Herrera et al., 1986, respectively).

An irrigation system was installed and each pot was fitted with a drip rate of 2 L $h^{-1}$ and a device for homogenizing water delivery over the entire surface of the substrate. Two fertilization conditions were studied in this assay, 100% and 50% of the total of the fertilizer.

The fertilization consisted on one part of a basic dressing (500 kg/$ha^{-1}$), using a commercial fertilizer, the composition of which consisted of: 7% total N (5% ammoniacal N, 2% ureic N); 10% phosphorus (4% water soluble); 6% potassium; 25% sulfur and 2% magnesium, and on the other part, throughout the experiment, a fertirrigation solution of pH 7.90, electric conductivity 2106 mmhos/$cm^{-1}$, and total soluble solids 0.93 g/$l^{-1}$, $KNO_3$ (15,000 g), $Ca(NO_3)_2$ (1,000 g), $H_3PO_4$ (508 g), $HNO_3$ (452 g) was applied twice a week. In the case of the treatments with 50% fertilization, these received half of the basic dressing (250 kg/$ha^{-1}$) and half of the nutrients of the fertirrigation solution at the same frequency as the plants watered with 100% of the dose. Irrigation was applied equally in all treatments (3 times per week).

An experimental design which consisted of 8 treatments, 10 pots per treatment and 3 plants per pot was used. The studied treatments were the type of strain of mycorrhiza-forming fungus and an untreated control, versus two doses of fertilizer, 100% and 50%.

The studied treatments were:

T1. *Glomus mosseae* (100% Fertilization).
T2. *Glomus intraradices* (100% Fertilization).
T3. *Glomus iranicum* var. *tenuihypharum* var. nov. (100% Fertilization).
T4. Control (100% Fertilization).
T5. *Glomus mosseae* (50% Fertilization).
T6. *Glomus intraradices* (50% Fertilization).
T7. *Glomus iranicum* var. *tenuihypharum* var. nov. (50% Fertilization).
T8. Control (50% Fertilization).

The amount of the *Glomus iranicum* var. *tenuihypharum* var. nov. fungus present in the treatments in which the fungus was inoculated has been estimated. Between 1 and 5 grams of mycelium-spores of this species was produced in 1 kg of soil, which is a range between 0.1 and 0.5%. On the other hand, the root system in which it is produced, reached 10% of the gross weight (100 g). Fine rootlets, which are those associated with the mycorrhiza-forming fungus and these were 40 g per 1 kilogram of soil, i.e. 4% of the total weight. From these fine rootlets, only 75% has mycorrhizal propagules, therefore, the percentage of mycorrhizae in one kilogram of soil was equivalent to 3%.

Mycorrhizal development was studied by analyzing the roots of 5 plants per treatment after 75 days of treatment application. These roots were washed with water and a method based on non-vital staining with trypan blue was used for their detection. This method allowed comparing the amount of living fungal biomass within the mycorrhizal system. In all cases the samples were observed in an Olympus microscope (CX21).

Extramatrical mycelium was measured by estimating the amount of mg present in a given area from a correction factor. Easily extractable Glomalin was also detected.

The leaf fresh weight (LFW), leaf dry weight (LDW) and the root fresh weight (RFW) and root dry weight (RDW) were assessed within 90 days of the start of the treatments. For this study, 5 plants per treatment were collected and they were separated into different organs and weighed on a Sartorius model balance. For the dry weight, the samples were placed in an oven at 80° C. to constant weight.

The gas exchange parameters (net photosynthesis, $A_n$ and stomatal conductance, $G_s$) were measured in 10 plants per treatment, using the LICOR LI-6400 Portable Photosynthesis System (LI-COR Inc., Lincoln, Nebr., USA model. LI-6400). All measurements were performed at solar noon and twice during the assay period (40 and 75 days). The efficiency of water use (WUE) was determined by the An/Gs ratio.

Chlorophyll measurement, in SPAD units, was measured in 10 plants twice (40 and 75 days) for the duration of the assay. It was determined with a portable meter (Chlorophyll meter SPAD-502, Konica Minolta). The apparatus carried out instantaneous and non-destructive measurements, called relative chlorophyll index (RCI, SPAD units), which indicates an absorbance value of the maximum wavelength range at 650 nm (red) emitted by the leaves, which is a high absorbance region due to the chlorophyll molecules.

The data of ion content in the leaves were obtained by the ICP-OES technique (Iris Intrepid II XDL, OribaSci.) in the Ionomics service of the CEBAS-CSIC, Murcia, within 75 days of the start of treatment.

The ions measured were:

Macroelements: Nitrogen (N), Phosphorus (P), Potassium (K) and Calcium (Ca)

Trace elements: Manganese (Mn), Iron (Fe) and Zinc (Zn).

Ions determination was performed on dry and ground material until reaching a particle size capable of passing through a sieve of 0.5 mm mesh diameter and stored in plastic containers until subsequent chemical analysis.

Table 3 shows the results obtained in the evaluation of mycorrhizal activity of the three strains under study in the presence of the two doses of fertilizers. A quick analysis of the results shows that in any of the situations of fertilization used the mycorrhiza-forming fungi have greater expression in terms of mycorrhizal colonization, mycelium and Glomalin production, compared to controls which, since they had natural agricultural soil, have mycorrhiza-forming fungi, but with generally lower values in the presence of the fertilization doses used.

In the analyses of individual parameters, we can see that for the case of internal mycorrhizal colonization, the highest values are in the strains of mycorrhiza-forming fungi and within these the *Glomus iranicum* var. *tenuihypharum* var. nov. strain, from a sodium-saline soil, significantly stands out reaching the highest values in the plants treated with 100% of the dose of fertilizer (78%) although it is not significantly different from its 50% counterpart (70%). However, this behavior was not observed for the two remaining strains.

Both *Glomus mosseae* and *Glomus intraradices* reached their greatest internal presence in the presence of lower doses of fertilizers (43 and 53.7%, respectively), but against higher doses of fertilization these values dropped to 21.24 and 24.0% respectively, very close to the values reached by the control under these conditions (Table 3).

TABLE 3

Extramatrical mycelium (mg/kg$^{-1}$), Mycorrhizal colonization (%) and easily extractable Glomalin concentration (mg/g$^{-1}$ soil) in lettuce plants inoculated with *Glomus mosseae* (G.m), *Glomus intraradices* (G.i) and *Glomus iranicum* var *tenuihypharum* var. nov. (*G. iranicum*) and untreated (C) after 75 days in cultivation with fertilization of 100% and 50%.

| | Extramatrical mycelium (mg · kg$^{-1}$ s) | Mycorrhizal colonization (%) | Glomalin (mg · g$^{-1}$ soil) |
|---|---|---|---|
| G.m 100% | 143.0 ± 17.8 e | 21.25 ± 1.5 d | 133.0 ± 2.1 d |
| G.i 100% | 232.0 ± 13.9 d | 24.0 ± 6.7 d | 323.3 ± 1.6b |
| *G. iranicum* 100% | 850.0 ± 19.9 a | 78.7 ± 1.63 a | 467.1 ± 5.6 a |
| C 100% | 122.2 ± 13.9 e | 12.75 ± 1.0 e | 90.10 ± 7.7 e |
| G.m 50% | 221.2 ± 11.2 d | 43.0 ± 3.78 c | 209.7 ± 4.5 c |
| G.i 50% | 345.5 ± 12.9 c | 53.75 ± 1.0 b | 345.0 ± 7.7 b |
| *G. iranicum* 50% | 765.9 ± 11.2 b | 70.0 ± 1.46 a | 422.3 ± 9.8 a |
| C 50% | 155.4 ± 15.9e | 9.25 ± 0.69 e | 100.6 ± 9.9de |
| Es x | 10.23*** | 6.83*** | 8.4*** |

\*\*\*Indicate the significance level of 0.001. Different letters in the same columns correspond to significantly different values. According to the Duncan's multiple comparison test (P < 0.05).

The extramatrical mycelium surprisingly showed extreme differences among the types of fungal species in the two fertilization conditions studied. Again, the species isolated from sodium-saline soil, (*Glomus iranicum* var. *tenuihypharum* var. nov.), expressed the highest values of ectophyte mycomass, reaching values of 850 mg/kg soil in the presence of the highest dose of fertilizer, in this case significantly different with the lowest dose of fertilizer, 765.9 mg/kg soil. However compared to the other treatments, the differences were very significant. In this case the remaining strains had higher yield than untreated controls in any of the situations, the best significantly different combination being when the plants had 50% of chemical fertilization. When the strains faced the higher dose they had lower development and even in the case of *Glomus mosseae* it developed low levels of mycelium, comparable with the native strains, which had a low yield.

This effect was also observed in the production of Glomalin easily extractable from the soil. In this case and as a consequence of the ectophyte mycorrhizal activity, the highest values of Glomalin, which is an insoluble glycoprotein secreted by the extramatrical mycelium of mycorrhiza-forming fungi, were reached in those treatments with higher production of mycelium, consisting of almost a carbon copy of mycelium behavior. Again, the highest values were expressed in the presence of the *Glomus iranicum* var. *tenuihypharum* var. nov. strain; in this case there were no significant differences between the doses of fertilizer used with 467.1 (100%) and 422.3 (50%) mg/g soil and it was the species that excreted more protein into the medium, followed by the other two species that, again, expressed their greatest potential against lower doses of fertilizer (50%) with 345 mg/g soil for *Glomus intraradices* and 209 mg/g soil for *Glomus mosseae*.

This effect found in mycorrhizal activity was maintained in the evolution of chlorophyll concentrations and gas exchange measurements performed throughout the crop.

Table 4 and 5, show the results of evolution of the measurements of SPAD, Net photosynthesis (An), Stomatal conductance (Gs) and Efficiency in water use (W/Gs) at 40 and 75 days in the treatments inoculated with different strains of mycorrhiza-forming fungi and untreated plants against the 50% and 100% doses of chemical fertilization.

TABLE 4

SPAD, net photosynthesis (An) ($\mu$mol $CO_2$ m$^{-2}$ s$^{-1}$), stomatal conductance (Gs) (mmol $H_2O$ m$^{-2}$ s$^{-1}$) and efficiency in water use (WUE, $\mu$mol $CO_2$ mmol$^{-1}$ $H_2O$) in inoculated and control lettuce plants with 100% and 50% of fertilization (40 days).

| Treatments | SPAD | An ($\mu$mol $CO_2$ m$^{-2}$ s$^{-1}$) | Gs (mmol $H_2O$ m$^{-2}$ s$^{-1}$) | WUE (An/Gs) |
|---|---|---|---|---|
| G. mosseae 100% | 25.2 b | 8.23 c | 121 a | 68.01 c |
| G. intraradices 100% | 22.0 d | 8.12 c | 123 a | 66.0 c |
| G. iranicum 100% | 31.1 a | 10.33 a | 117 b | 88.29 a |
| Control 100% | 22.2 d | 7.3 d | 120 a | 60.83 d |
| G. mosseae 50% | 24.4 c | 9.4 b | 119 a | 78.99 b |
| G. intraradices 50% | 23.4 c | 9.21 b | 122 a | 75.49 b |
| G. iranicum 50% | 26.3 b | 10.66 a | 119 b | 89.57 a |
| Control 50% | 22.47 d | 7.34 d | 121 a | 60.66 d |
| Es x | 0.14*** | 0.42*** | 1.89*** | 2.25** |

\*\*\*Indicate the significance level of 0.001. Different letters in the same column correspond to significantly different values. According to the Duncan's multiple comparison test (P < 0.05).

The same as the mycorrhizal behavior, higher SPAD values compared with controls are obtained in the variants treated with different species of mycorrhizal fungi 40 days after planting the lettuces. The *Glomus iranicum* var. *tenuihypharum* var. nov. species had a SPAD value of 31, it promoted higher SPAD values against the highest dose of fertilizer in treated plants, constituting the highest production, followed by *Glomus mosseae*, with a SPAD value of 25; however in the case of the plants treated with *Glomus*

*intraradices* they displayed a contrary behavior, developing higher SPAD values against the 50% dose. However, this value indicates the indirect chlorophyll concentration and it can also be indicative of better nitrogen nutrition, but since it is an indirect measurement, it is not a variable indicating a particular functioning, but an indicator of the light concentration emitted by the leaf and related in turn with the plastids present in photosynthetic cells, thus its analysis should always be correlated with gas exchange.

In the remaining gas exchange parameters measured the photosynthesis values were always higher in the case of the strains of mycorrhiza-forming fungi and the plants treated with *Glomus iranicum* var. *tenuihypharum* var. nov., where the highest rates of $CO_2$ assimilation 10.33 (100%) and 10.66 (50%) were achieved in any of the variants and, in turn, the lowest rates of stomatal conductance 117 (100%) and 119 (50%), which ultimately express the highest values of efficient water use of 88.29 in the case of 100% fertilization and 89.27 against 50%.

These values increased after 75 days of cultivation (Table 5), where not only they were the highest again, but they had a higher photosynthetic activity in absolute terms at the expense of low stomatal conductance, derived from a proper physiological functioning and a much higher efficient use of water on the order of 106.3 in the case of 100% fertilization and 95.77 in the case of 50%.

TABLE 5

SPAD, net photosynthesis (An) ($\mu$mol $CO_2$ $m^{-2}$ $s^{-1}$), stomatal conductance (Gs) (mmol $H_2O$ $m^{-2}$ $s^{-1}$) and efficiency in water use (WUE, $\mu$mol $CO_2$ $mmol^{-1}$ $H_2O$) in inoculated and control lettuce plants with 100% and 50% of fertilization (75 days)

| Treatments | SPAD | An ($\mu$mol $CO_2$ $m^{-2}$ $s^{-1}$) | Gs (mmol $H_2O$ $m^{-2}$ $s^{-1}$) | WUE (An/Gs) |
|---|---|---|---|---|
| G. mosseae 100% | 20.2 b | 9.39 b | 140 a | 67.07 d |
| G. intraradices 100% | 19.0 c | 9.23 b | 140 a | 65.09 d |
| G. iranicum 100% | 28.1 a | 12.76 a | 120 b | 106.3 a |
| Control 100% | 19.1 d | 8.47 c | 125 a | 67.76 d |
| G. mosseae 50% | 21.28 b | 9.795 b | 133 a | 73.30 c |
| G. intraradices 50% | 20.41 c | 9.39 b | 132 a | 71.14 c |
| G. iranicum 50% | 23.1 b | 11.78 a | 123 b | 95.77 b |
| Control 50% | 21.66 c | 8.17 c | 125 a | 65.36 d |
| Es x | 0.25*** | 0.815*** | 2.4** | 1.80*** |

***Indicate the significance level of 0.001. Different letters in the same column correspond to significantly different values. According to the Duncan's multiple comparison test ($P < 0.05$).

The other strains were lower than *Glomus iranicum* var. *tenuihypharum* var. nov. on either fertilization conditions, and although they had a higher photosynthetic activity at 75 days, with respect to the previous evolution, they did it at the expense of increased stomatal conductivity, whereby they reached a less efficient use of water, compared not only with the *Glomus iranicum* var. *tenuihypharum* var. nov. strain, but also with their own behavior at 40 days, which may be related to a loss of the mycorrhizal activity itself, as previously noted with a drop of mycorrhizal colonization against higher fertilization doses.

Although the control treatments had a generally less efficient use of water at 40 days, this effect was different at the end of the cycle. In the case of the plants treated with 50% of fertilization, the control treatment was below the plants treated with mycorrhiza-forming fungi, but at 100% of fertilization, only the plants treated with *Glomus iranicum* var. *tenuihypharum* var. nov. had a more efficient use. The control efficiency reached its maximum (67.76), with no significant differences with the other two species of Arbuscular Mycorrhizal Fungi (AMF) (67.07 and 65.09), even in the case of *Glomus intraradices*. This value is lower than the control treatment although not significant, demonstrating a photosynthetic mismatch possibly derived from a symbiotic relationship not suitable for this stage of the crop.

Obviously this analysis of the physiological activity of the evaluated plants is closely related to productivity and the nutritional levels achieved in plants treated with AMF. Table 6 and 7, show the leaf and root fresh dry weights reached in the different treatments at harvest, as well as nutritional elements at 75 days of cultivation.

The analysis of leaf and root biomass show the positive effect of the application of AMF. Both under peak fertility conditions and under average conditions, the strains of mycorrhiza-forming fungi produced higher biomass, relative to their untreated counterparts, but in a different manner.

In the case of *Glomus iranicum* var. *tenuihypharum* var. nov. strain, following with its proper mycorrhizal functioning and the physiological potential it provided to the treated plants, it obtained the highest values of biomass both under one condition and the other; however, it reached the highest values with maximum fertilization (Table 5).

TABLE 6

Leaf Fresh Weight (g), Leaf Dry Weight (g), Root Fresh Weight (g) and Root Dry Weight (g) in lettuce plants inoculated with *Glomus mosseae* (G.m), *Glomus intraradices* (G.i) and *Glomus iranicum* var. *tenuihypharum* var. nov. (*G. iranicum*) and untreated (C) after 90 days in cultivation with 100% and 50% of Fertilization.

| Treatments | Leaf Fresh Weight (g) | Leaf Dry Weight (g) | Root Fresh Weight (g) | Root Dry Weight (g) |
|---|---|---|---|---|
| G. mosseae 100% | 600.42 ± 3.3 b | 9.18 ± 1.5 e | 122.28 ± 1.6 g | 1.7 ± 1.7 c |
| G. intraradices 100% | 613.68 ± 4.6 b | 10.71 ± 2.3 d | 162.83 ± 9.62 d | 1.6 ± 0.33 c |
| G. iranicum 100% | 800.03 ± 0.62 a | 17.19 ± 0.25 a | 232.13 ± 5.43 a | 2.89 ± 0.44 a |
| Control 100% | 678.26 ± 3.73 b | 9.12 ± 2.45 e | 179.51 ± 3.21 e | 1.4 ± 0.93 d |
| G. mosseae 50% | 770.42 ± 1.61 ab | 13.44 ± 0.35 c | 171.7 ± 3.74 c | 1.8 ± 0.12 c |
| G. intraradices 50% | 640.42 ± 2.55 b | 11.50 ± 1.19 c | 199.31 ± 4.74 b | 2.0 ± 0.45 a |
| G. iranicum 50% | 782.50 ± 2.18 a | 15.04 ± 0.41b | 203.13 ± 4.56 b | 2.2 ± 1.32 b |

TABLE 6-continued

Leaf Fresh Weight (g), Leaf Dry Weight (g), Root Fresh Weight (g) and
Root Dry Weight (g) in lettuce plants inoculated with *Glomus mosseae* (G.m), *Glomus
intraradices* (G.i) and *Glomus iranicum* var. *tenuihypharum* var. nov. (*G. iranicum*) and
untreated (C) after 90 days in cultivation with 100% and 50% of Fertilization.

| Treatments | Leaf Fresh Weight (g) | Leaf Dry Weight (g) | Root Fresh Weight (g) | Root Dry Weight (g) |
|---|---|---|---|---|
| Control 50% | 510.58 ± 1.58 c | 8.69 ± 1.2 e | 158.57 ± 1.66 f | 1.3 ± 1.41 d |
| Es x | 6.38*** | 1.76*** | 32.7*** | 0.6** |

***Indicate the significance level of 0.001. Different letters in the same column correspond to significantly different values. According to the Duncan's multiple comparison test ($P < 0.05$).

However, the remaining strains obtained their greatest development potential in the treatments fertilized with 50% of the fertilizer, reducing their productivity as the levels of fertilizer were increased in the soil solution. In the case of the untreated controls, the highest biomass values were expressed in the presence of the highest doses of fertilizers.

The analysis of foliar nutrient concentrations observed at 75 days of cultivation confirmed the results obtained in the other variables studied (Table 6). In this case, in most of the elements significant differences were found between the studied treatments except K and Zn leaf contents. Again, this time the highest values appear in the treatments that reached the greatest development in biomass and physiological activity, highlighting the plants treated with *Glomus iranicum* var. *tenuihypharum* var. nov. species, in the presence of the highest dosage of fertilizers.

It is important to highlight the values of the trace elements Fe (constituent of chlorophyll) and Mn (Enzyme Cofactor of the process of photosynthesis and growth activity in general) found, closely related to the photosynthetic activity of the plants. Their high expression in plants treated with *Glomus iranicum* var. *tenuihypharum* var. nov., significantly different from the rest of the plants treated or not with AMF, indicates not only a strong response to the absorption of this element, but also a need of the symbiosis for raising their concentrations in response to an increased photosynthetic activity in general.

The rest of the elements followed the tendency found in the remaining analyzed variables, the highest nutrient levels appearing in plants treated with 50% of fertilization for strains treated with *Glomus intraradices* and *Glomus mosseae* strains, but when the fertilization was higher, these values were matched even with the control treatments, indicating a low effectiveness on the absorption of these elements under conditions of high doses of salts in the nutrient solution.

The AMF species *Glomus iranicum* var. *tenuihypharum* var. nov., previously isolated from a sodium saline ecosystem with pH 8.4 and a high concentration of Ca and Mg showed high effectiveness against high salt concentrations in the nutrient solution, differing not only from controls where one might expect lower response but also compared with other species of mycorrhiza-forming fungi which were not only lower, but their effectiveness in fertilization conditions at 100% was diminished, even for some variables, lower than the control.

TABLE 7

Concentrations of some nutritional elements (ppm) in lettuce plants
inoculated with *Glomus mosseae* (G.m), *Glomus intraradices* (G.i) and
*Glomus iranicum* var. *tenuihypharum* var. nov. (*G. iranicum*) and
untreated (C) after 75 days of cultivation with 100% and 50% of fertilization.

| | N (ppm) | P (ppm) | K (ppm) | Ca (ppm) | Mn (ppm) | Fe (ppm) | Zn (%) |
|---|---|---|---|---|---|---|---|
| G.m 100% | 2.2 c | 0.12 c | 5.9 | 2.3 c | 130.2 c | 322 b | 23.4 |
| G.i 100% | 2.1 c | 0.11 d | 5.9 | 2.4 c | 132.2 c | 342 b | 22.1 |
| *G. iranicum* 100% | 2.9 a | 0.14 a | 6.5 | 3.2 a | 167.4 a | 750 a | 34.2 |
| C 100% | 2.4 c | 0.11 d | 5.8 | 2.9 b | 133.5 c | 389 b | 30.2 |
| G.m 50% | 2.5 bc | 0.11 d | 5.6 | 2.1 c | 125.2 d | 343 b | 33 |
| G.i 50% | 2.6 b | 0.13 a | 5.7 | 2.1 c | 134.2 c | 332 b | 32 |
| *G. iranicum* 50% | 2.8 a | 0.13 a | 5.6 | 2.4 c | 146.9 b | 688 a | 36.4 |
| C 50% | 2.2 c | 0.11 d | 5.5 | 2.0 c | 122.3 d | 399 b | 28.9 |
| Es x | 0.02** | 0.03** | 1.1 n.s | 0.02** | 8.9*** | 11.2** | 7.8 n.s |

, * and ns indicate the significance level of 0.05, 0.001, not significant, respectively. Different letters in the same column correspond to significantly different values. According to the Duncan's multiple comparison test ($P < 0.05$).

The invention claimed is:

1. A method for biostimulating, regulating or enhancing plant growth comprising applying an effective amount of a composition comprising a strain of *Glomus iranicum* var. *tenuihypharum* var. nov. deposited under BCCM deposit number 54871 comprising the sequence identified by SEQ ID NO: 1 and 2:1 smectite clays.

2. The method according to claim 1, wherein said 2:1 smectite clays are dioctahedral or trioctahedral.

3. The method according to claim 1, wherein said 2:1 smectite clays are selected from the group consisting of sepiolite, attapulgite, nontronite and saponite.

4. The method according to claim 1, wherein the concentration of said *Glomus iranicum* var. *tenuihypharum* var. nov. strain is between 0.05 and 4% by weight.

5. The method according to claim 4, wherein said concentration is between 0.1 and 3% by weight.

6. The method according to claim 1, wherein the composition is in a form of powder, emulsifiable concentrate or granules.

7. The method according to claim 1, wherein the composition is a liquid, a solid or a gel.

8. The method according to claim 1, wherein the composition further comprises at least one fungicide, at least one bio-fungicide, at least one insecticide, at least one bio-insecticide, at least one nematicide and/or at least one bio-nematicide.

9. The method according to claim 8, wherein said fungicide is selected from the group consisting of manganese ethylene-1,2-bisdithiocarbamate, polymer, ethylene bisdithiocarbamate (EBDC), methyl N-(methoxyacetyl)-N-(2,6-xylyl)-DL-alaninate, 2-(4-Chlorophenyl)-2-(1,2,4-triazol-1-ylmethyl)hexanenitrile, 1, 2, 4-trichloro-3,5-dinitrobenzene, propyl [3-(dimethylamino)propyl]carbamate, quintozene, streptomycin, sulfur, thiophanate-methyl, thiram, triforine, vinclozolin, zinc white, zineb, ziram, etridiazole and thiophanate-methyl, fixed copper, chlorothalonil, captan, chloroneb, cyproconazole, zinc ethelene, bisdithiocarbamate, etridiazole, fenaminosulf, fenarimol, flutolanil, folpet, fosetyl- Al and iprodione.

10. The method according to claim 8, wherein said bio-fungicide is selected from the group consisting of *Trichodermas* sp, *Bacillus subtilis*, *Bacillus licheniformis*, *Bacillus pumilus*, *Bacillus amyloliquefaciens*, *Streptomyces* sp, *Coniothyrium minitans* and *Pythium oligandrum*.

11. The method according to claim 8, wherein said insecticide is selected from the group consisting of organophosphate, carbamate and neonicotinoid.

12. The method according to claim 8, wherein said bio-insecticide is selected from the group consisting of *Bacillus* sp. *Chromobacterium* sp., *Beauveria* sp. and *Metarhizium* sp.

13. The method according to claim 8, wherein said nematicide is organophosphate or carbamate.

14. The method according to claim 8, wherein said bio-nematicide is *Pasteuria* sp.

15. The method according to claim 1, wherein said composition is applied at a location of said plant selected from the group consisting of root, shoot, stem, one or more leaves, one or more flowers and fruit.

16. The method according to claim 1, wherein the composition is applied with a fertilizer.

17. The method according to claim 1, wherein the composition is applied to the plant through seed treatment, root treatment, roots embedded in an emulsion, addition to irrigation water, irrigation, application of powder to the root system or application of emulsion injected into the root system.

* * * * *

SEQUENCE LISTING

```
<160> NUMBER OF SEQ ID NOS: 1

<210> SEQ ID NO 1
<211> LENGTH: 813
<212> TYPE: DNA
<213> ORGANISM: Glomus iranicum var. tenuihypharum var. nov.
<220> FEATURE:
<221> NAME/KEY: source
<222> LOCATION: 1..813
<223> OTHER INFORMATION: /mol_type="unassigned DNA"
      /note="18S (partial sequence)-ITS1 (complete sequence)-5.8S
      (partial sequence)"
      /organism="Glomus iranicum var. tenuihypharum var. nov."

<400> SEQUENCE: 1
cctgcggctt atttgactca acacggggaa actcaccagg tccagacata gtaaggattg      60
acagattgag agctctttct tgattctatg ggtggtggtg catggccgtt cttagttggt     120
ggagtgattt gtctggttaa ttccgttaac gaacgagacc ttaacctgct aaatagctag     180
gcttaacttc ggttaggtcg tcagcttctt agagggacta tcggtgttta accgatggaa     240
gtttgaggca ataacaggtc tgtgatgccc ttagatgttc tgggccgcac gcgcgctaca     300
ctgatgaagt catcgagttc atttccttta tcggaagata tgggtaatct tttgaaactt     360
catcgtgctg gggatagagc tttgcaatta ttgctcttaa acgaggaatc cctagtaagc     420
acaagtcatc agcttgtgct gattacgtcc ctgcccttttg tacacaccgc ccgtcgctac    480
taccgattga atggcttagt gaggccctcg gatcgacgct cggagactgg caacagtttc     540
cgttcgttga gaagttggtc aaacttggtc atttagagga agtaaaagtc gtaacaaggt     600
ttccgtaggt gaacctgcgg aaggatcatt attgatttag cgaaccgagc gttagcgagg     660
ttctgcgatc gcttatattt aaaacccact cttaacgtat aaaattttta ttaatgatga     720
aaaaaaatag atcactctat aaaatcggaa aacccgctta aaatttttta tgtctttcga    780
atagataaaa aaaatatca ctttcaacaa cgg                                  813
```